(12) United States Patent
Dorian et al.

(10) Patent No.: US 12,220,512 B2
(45) Date of Patent: Feb. 11, 2025

(54) PLASMA/CELL CONCENTRATOR APPARATUS AND METHODS

(71) Applicant: Hanuman Pelican, Inc., New Orleans, LA (US)

(72) Inventors: Randy Dorian, San Diego, CA (US); Michael D. Leach, Warsaw, IN (US); Richard W. Storrs, Berkeley, CA (US)

(73) Assignee: Hanuman Pelican, Inc., New Orleans, LA (US)

( * ) Notice: Subject to any disclaimer, the term of this patent is extended or adjusted under 35 U.S.C. 154(b) by 914 days.

(21) Appl. No.: 17/179,844

(22) Filed: Feb. 19, 2021

(65) Prior Publication Data

US 2021/0330873 A1    Oct. 28, 2021

Related U.S. Application Data (60) Provisional application No. 63/014,291, filed on Apr. 23, 2020.

(51) Int. Cl.
*A61M 1/34* (2006.01)
*B04B 5/04* (2006.01)

(52) U.S. Cl.
CPC ......... *A61M 1/3486* (2014.02); *B04B 5/0442* (2013.01); *B04B 2005/0478* (2013.01); *B04B 2005/0485* (2013.01)

(58) Field of Classification Search
CPC ................ A61M 1/3486; A61M 5/178; A61M 2039/229; A61M 2205/7545; B04B 5/0442; B04B 2005/0478; B04B 2005/0485; G01N 33/491; B01L 2200/16; B01L 2300/0681; B01L 2400/0478; B01L 2400/0622; B01L 3/5635
USPC ........ 210/767, 645, 650, 782, 455, 435, 287
See application file for complete search history.

(56) References Cited

U.S. PATENT DOCUMENTS

| | | |
|---|---|---|
| 5,585,007 A | 12/1996 | Antanavich et al. |
| 5,788,662 A | 8/1998 | Antanavich et al. |
| 6,063,297 A | 5/2000 | Antanavich et al. |
| 6,214,338 B1 | 4/2001 | Antanavich et al. |
| 6,905,612 B2 | 6/2005 | Dorian et al. |
| 7,553,413 B2 | 6/2009 | Dorian et al. |
| 7,708,152 B2 | 5/2010 | Dorian et al. |
| 7,824,559 B2 | 11/2010 | Dorian et al. |

(Continued)

FOREIGN PATENT DOCUMENTS

| | | |
|---|---|---|
| EP | 0733378 | 9/1996 |
| EP | 2077115 | 7/2009 |

(Continued)

*Primary Examiner* — Madeline Gonzalez
(74) *Attorney, Agent, or Firm* — Levine Bagade Han LLP (57) ABSTRACT

Plasma/cell concentrator apparatus and methods are described herein for concentrating constituents from a fluid. Generally, a volume of the fluid may be urged from a first reservoir to a second reservoir through a fluid channel and a volume of desiccant for mixing with the fluid may be introduced to create a mixture. This fluid and desiccant mixture may be passed between the first and second reservoirs until one or more components from the fluid are absorbed by the desiccant. After mixing, the fluid may be withdrawn through a withdrawal channel which is in fluid communication with the fluid channel while preventing the desiccant from passing into the withdrawal channel.

8 Claims, 11 Drawing Sheets

(56) References Cited

U.S. PATENT DOCUMENTS

| | | |
|---|---|---|
| 7,866,485 B2 | 1/2011 | Dorian et al. |
| 7,901,584 B2 | 3/2011 | Dorian et al. |
| 7,987,995 B2 | 8/2011 | Dorian et al. |
| 8,096,422 B2 | 1/2012 | Dorian et al. |
| 8,105,495 B2 | 1/2012 | Dorian et al. |
| 8,133,389 B2 | 3/2012 | Dorian et al. |
| 2004/0182788 A1 | 9/2004 | Dorian et al. |
| 2009/0247985 A1* | 10/2009 | Melsheimer .......... A61J 1/2096 604/506 |
| 2009/0292290 A1 | 11/2009 | Truckai et al. |
| 2010/0206798 A1 | 8/2010 | Dorian et al. |
| 2014/0071787 A1* | 3/2014 | Leach .................... B01F 21/22 366/183.2 |
| 2015/0101995 A1 | 4/2015 | Kim |
| 2017/0258877 A1 | 9/2017 | Bare et al. |

FOREIGN PATENT DOCUMENTS

| | | |
|---|---|---|
| EP | 2863221 | 4/2015 |
| WO | WO2009/002849 | 12/2008 |
| WO | WO2021/216177 | 10/2021 |

* cited by examiner

PLASMA/CELL CONCENTRATOR APPARATUS AND METHODS

This application claims the benefit of priority to U.S. Prov. App. 63/014,291 filed Apr. 23, 2020, which is incorporated herein by reference in its entirety.

FIELD OF THE INVENTION

The present invention relates to apparatus and methods for concentrating blood components. More particularly, the present invention relates to apparatus and methods for effectively concentrating macromolecular plasma constituents and/or cells from blood plasma or platelet rich plasma with or without white blood cells without requiring centrifugation.

BACKGROUND OF THE INVENTION

Blood may be fractionated and the different fractions of the blood used for different medical needs. For instance, anemia (low erythrocyte levels) may be treated with infusions of erythrocytes. Thrombocytopenia (low thrombocyte (platelet) levels) may be treated with infusions of platelet concentrate.

The sedimentation of the various blood cells and plasma is based on the different specific gravity of the cells and the viscosity of the medium. When sedimented to equilibrium, the component with the highest specific gravity (density) eventually sediments to the bottom, and the lightest rises to the top. Under the influence of gravity or centrifugal force, blood spontaneously sediments into three layers. At equilibrium the top, low-density layer is a straw-colored clear fluid called plasma. Plasma is a water solution of salts, metabolites, peptides, and many proteins ranging from small (insulin) to very large (complement components). Plasma per se has limited use in medicine but may be further fractionated to yield proteins used, for instance, to treat hemophilia (factor VIII) or as a hemostatic agent (fibrinogen). The term platelet rich plasma (PRP) is used for this component because most of the plasma proteins and platelets in the whole blood are in the plasma following slow centrifugation so the concentration of platelets in the plasma has increased while suspended in supernatant plasma. The uppermost layer after centrifugation typically contains plasma proteins only and is typically called platelet-poor plasma (PPP) due to the absence or low number of platelets as a result of a "hard spin".

The bottom, high-density layer is a deep red viscous fluid comprising a nuclear red blood cells (RBC) specialized for oxygen transport. The red color is imparted by a high concentration of chelated iron or heme that is responsible for the erythrocytes high specific gravity. Packed erythrocytes, matched for blood type, are useful for treatment of anemia caused by, e.g., bleeding. The relative volume of whole blood that consists of erythrocytes is called the hematocrit, and in normal human beings can range from about 38% to about 54%.

The intermediate layer is the smallest layer, appearing as a thin white band on top the erythrocyte layer and below the plasma, and is called the buffy coat. The buffy coat itself has two major components, nucleated leukocytes (white blood cells) and a nuclear smaller bodies called platelets (or thrombocytes). Leukocytes confer immunity and contribute to debris scavenging. Platelets seal ruptures in the blood vessels to stop bleeding and deliver growth and wound healing factors to the wound site. The buffy coat may be separated from whole blood when the blood is subjected to a "hard spin" in which the whole blood is spun hard enough and long enough so that platelets sediment from plasma onto packed red cells and white cells percolate up through red cell pack to the interface between red cells and plasma.

In order to separate a volume of blood into its constituent components, centrifugation equipment is typically required to separate and concentrates the components. Other methods for concentrating blood components, particularly plasma macromolecular constituents and/or platelets and/or white blood cells, have included devices employing swept hollow fiber filtration to remove water and low molecular weight solutes from plasma or PRP. Other devices have use dry size-exclusion chromatographic beads to absorb water and low molecular weight solutes in a centrifuge tube. These devices have included a paddle or rake to stir the plasma/bead mix during concentration, followed by removal of the beads by centrifugation into a lower or distal compartment of the centrifuge tube (or drum) through a frit (e.g., filter having a known porosity which is comprised of sintered particles of glass, ceramic, etc.) which retains the swollen beads while allowing concentrated product to pass through.

Yet other methods have included devices which use beads contained in a syringe together with an agitator, such as one or more metal BBs to facilitate mixing of the plasma with the beads, followed by expression of the concentrated product through a bead-retaining frit or centrifugation through a bead retaining frit.

With all of these methods, some means of sweeping or agitation is typically needed to prevent formation of a gel polarization membrane on the surface of the beads or fibers. In the case of the hollow fibers, plasma is circulated through the fibers during filtration to sweep the membrane surface. In the case of a centrifugal device, agitation is provided by the paddle or rake. In the case of the bead-loaded syringe, agitation is achieved by shaking the syringe so that the BB is able stir the bead/plasma slurry.

Hollow fiber cartridges are generally expensive and methods using them usually involve circulating pumps and tubing circuits. When using chromatographic beads, the beads must be mixed immediately after contacting plasma with the beads, both to prevent gel polarization which can clog the bead pores while depositing large molecules on their surfaces and also to prevent the beads from clumping together as a consequence of high protein concentrations accumulating on the surfaces.

Accordingly, there remains a need for simple and effective methods and devices for effectively concentrating macromolecular plasma constituents and/or cells from blood plasma or PRP with or without white blood cells without requiring centrifugation.

SUMMARY OF THE INVENTION

The present invention relates to apparatus and methods for effectively concentrating macromolecular plasma constituents and/or cells from blood plasma or PRP with or without white blood cells without requiring centrifugation. One variation of the apparatus may utilize a first syringe fluidly coupled to a second syringe via a manifold which also provides receiving channels to temporarily or permanently secure the tips of the respective syringes to the manifold. Each of the syringes may be integrated directly with the manifold or optionally fitted with non-standard couplings to ensure that one or both syringes cannot be inadvertently detached or attached to an incorrect port.

A fluid channel may extend through the manifold to fluidly couple the openings of the first syringe and second syringe and a withdrawal channel may extend through the manifold to fluidly couple to the fluid channel. An actuatable valve which may be configurable between an open and closed configuration, e.g., automatically or manually via a stopcock, may be incorporated with the withdrawal channel to prevent the release of fluid from the fluid channel. A filter or frit may also be incorporated into the manifold at the entry of the withdrawal channel to filter select components from passing into the withdrawal channel from the fluid channel.

The fluid channel may optionally incorporate a number of projections or features such as vanes, spikes, crosshairs, etc., to facilitate the effective mixing of fluids as they pass through the fluid channel. Additionally, a volume of desiccating beads or elements may also be added within the fluid channel or directly within one or both of the syringes.

A volume of blood plasma or PRP to be concentrated may be introduced within the first syringe or second syringe (or both) and the syringes may be coupled to their respective ends in the manifold such that their openings are positioned at each end of the fluid channel. With the volume of desiccating beads retained within the fluid channel and/or within one or both syringes the respective plungers may be actuated in an alternating manner to push the blood plasma or PRP back-and-forth between the syringes through the fluid channel. As the blood plasma or PRP is cycled between the syringes, the withdrawal channel may remain closed to prevent leakage from the fluid channel. As the blood plasma or PRP cycles between the syringes through the fluid channel, it may become concentrated as the volume of beads mixes thoroughly with the blood plasma or PRP and absorbs various components within the blood plasma or PRP such as water, electrolytes and small proteins, thus leaving a platelet-rich plasma concentrate. Because the mixture of the beads and blood plasma or PRP is cycled back-and-forth between the syringes, the syringe connections to the manifold may be integral to ensure a fluid-tight connection and the internal diameter of the syringe couplings may be tapered internally at their proximal ends to reduce the likelihood of clogging due to any bead clumps which may be formed by gel polarization.

Once the blood plasma or PRP has been sufficiently concentrated, the valve along the withdrawal channel may be opened to allow for the withdrawal of the concentrated product as it passes through the fluid channel. The filter or frit may prevent the passage of the beads or other components into the withdrawal channel thus allowing only the concentrated product to pass through withdrawal channel and into a reservoir such as a collection syringe. The withdrawal channel may be opened to allow for the removal of the concentrated product as the bead and blood plasma or PRP mixture continues to cycle through the fluid channel. This ensures that the concentrated product may be harvested uniformly from the mixture. Also, sweeping of the bead surfaces during product extraction further ensures that if the beads are not yet fully saturated, any residual water absorption does not cause gel polarization and loss of macromolecular constituents or clumping.

Alternatively, both plungers in each respective syringe may be simultaneously pressed to create pressure to force the concentrated product from both syringes and through the withdrawal channel for collection with the valve opened. In any case, the filter or frit may prevent the beads from passing into the withdrawal channel so that only the concentrated product may pass through.

In an alternative variation, an additional withdrawal channel and port may be provided so that the material can be introduced without having to pass through the filter or frit. As the material is introduced through the manifold, it may mix with the beads contained within and sweep them into one or both of the syringes forcing the respective plungers to extend partially.

These beads may function as a concentrator when contacting and mixing with the blood plasma or PRP and may comprise any number of materials which are configured to selectively absorb particular components such as water, electrolytes, small proteins, etc. leaving a concentrated product for collection. Examples of various materials that the beads may be fabricated from may include any suitable material for processing the biological materials such as various polymers, metals, minerals, polysaccharides, silica gel, ceramics, glasses, etc.

In another variation, the manifold may include a manifold body which includes respective ports positioned on opposite ends of the manifold body for fluidly connecting to one another via fluid channel extending through the manifold body and between the ports. A withdrawal channel may extend from the fluid channel through a filter or frit positioned to prevent or inhibit any beads or other components from passing through and into the withdrawal channel.

A number of optional configurations are possible, for example, one of the two in-line syringes may be fitted with a biasing element such as a spring so that mixing can be effectuated by alternately applying and releasing pressure on only one syringe. The two syringes need not be parallel, but may be connected via a connecting manifold which adjoins them at any angle relative to each other. A second modified syringe may be coupled to the opposing port of the manifold body but rather than having a plunger, the second syringe may contain the biasing element within and anchored between the movable plunger and an anchoring platform which may be securely positioned relative to the body of the syringe.

In yet another embodiment, a volume of blood plasma or PRP may be concentrated by connecting a first syringe to a second syringe via a manifold containing a filter or frit and the first syringe may be optionally preloaded with a volume of beads while the second syringe may contain a volume of blood plasma or PRP to be concentrated. In other variations, the volume of beads may instead be preloaded within the manifold itself. The manifold or the second syringe may include a valve such as a stopcock which may be initially closed to prevent communication between the first and second syringes when initially coupled to the manifold.

With the plunger of the first syringe initially fully depressed, the plunger may be pulled proximally with the valve closed such that a vacuum force is created within the first plunger. This also allows for the volume of beads contained within to be dispersed within the syringe prior to contacting the fluid contained within the second syringe. The first plunger may be locked into its retracted position via a locking mechanism and the valve may be opened so that the vacuum within the first syringe may pull the fluid in through the manifold from the second syringe. This sudden dispersion of fluid into the first syringe may help to minimize any likelihood of clumping of the beads within the first syringe upon initial fluid contact and may also facilitate the rapid introduction of the fluid after the valve is opened. Once the fluid has been introduced into the first syringe, the locking mechanism may be released (e.g., by twisting the plunger rod relative to the syringe body) and the cycling of the slurry between the two syringes may be accomplished.

An alternative manifold body may have a first port and a second port both positioned along a first surface of the manifold such that the ports are in proximity to one another and fluidly connected via curved or angled fluid channels. An optional chamber may be incorporated between the fluid channels for holding a volume of beads within during the initial mixing phase between the syringes. Additionally, a filter or frit well may also be defined to extend from the chamber for retaining the frit within the chamber as well as allowing for a withdrawal syringe to be coupled to the manifold body. Because the ports are located along a common surface of the manifold body, the syringes may be angled relative to one another and relative to the manifold body in any number of angles. Furthermore, this variation may be utilized with any of the devices and methods described herein.

In yet another variation for recovering a volume of concentrated product, the coupling may be used in combination with a centrifuge rather than withdrawing the concentrated product directly from the manifold. The coupling may have a housing with an introduction port positioned upon an upper portion of the housing into which a mixed slurry may be introduced. A withdrawal port may be positioned upon a lower portion of the housing and a fit may be positioned within the housing to separate the internal volume into an upper portion and a lower portion.

With the mixed slurry introduced through the port and into the upper portion of housing, both ports may be capped or closed and entire coupling may undergo centrifugation to drive the fluid from the upper portion, through the frit, and into the lower portion of the housing. Once all concentrated product has been separated into the lower portion and the beads remaining within the upper portion above the fit, the withdrawal port may be opened to withdraw the concentrated product from the housing.

In one variation of a method for concentrating constituents from a fluid, the method may generally comprise urging a volume of the fluid from a first reservoir to a second reservoir through a fluid channel and introducing a volume of desiccant for mixing with the fluid. This fluid and desiccant mixture may be passed between the first and second reservoirs until one or more components from the fluid are absorbed by the desiccant. After mixing, the fluid may be withdrawn through a withdrawal channel which is in fluid communication with the fluid channel while preventing the desiccant from passing into the withdrawal channel.

In one variation of an apparatus for concentrating constituents from a fluid, the apparatus may generally comprise a connector having a first port and a second port connected via a fluid channel, a first reservoir having a variable pressure attachable to the first port, and a second reservoir having a variable pressure attachable to the second port. A withdrawal channel may be in fluid communication with the fluid channel and a filter may be positioned to prevent passage of a desiccant from the fluid channel into the withdrawal channel.

DETAILED DESCRIPTION OF THE INVENTION

Figure 1:
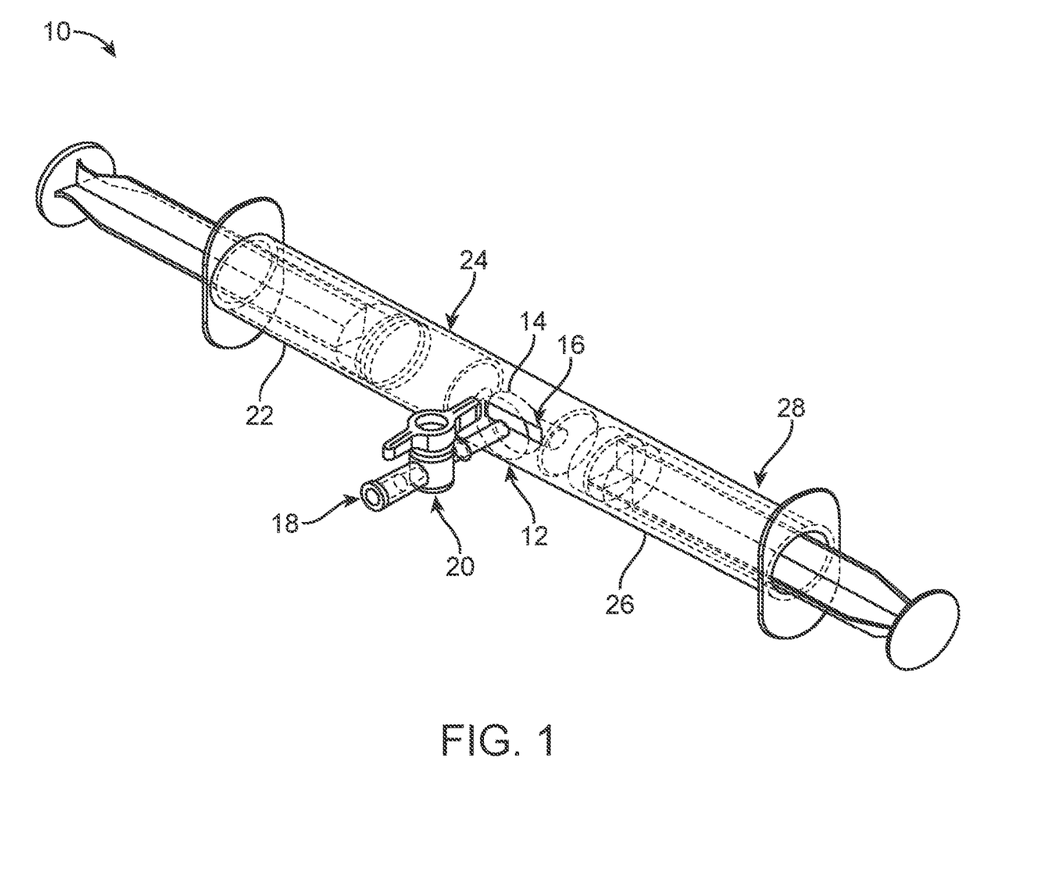
FIG. 1 shows a perspective view of an assembly used to effectively concentrate plasma constituents and/or cells without requiring centrifugation.
Figure 2A:
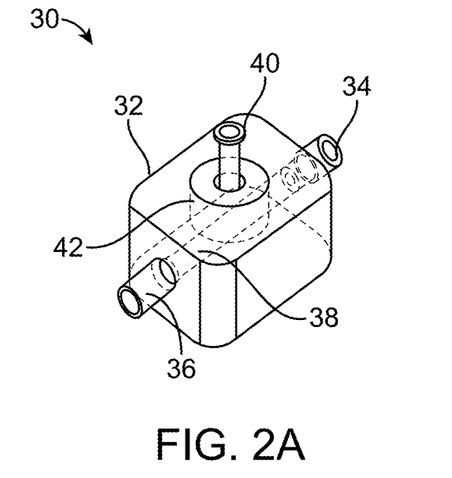
FIGS. 2A to 2D show perspective, side, bottom, and top views, respectively, of another manifold variation which may be used with conventional syringes or modified syringes.
Figure 2B:
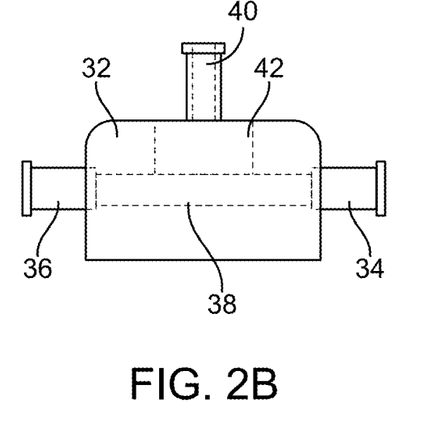
Figure 2C:
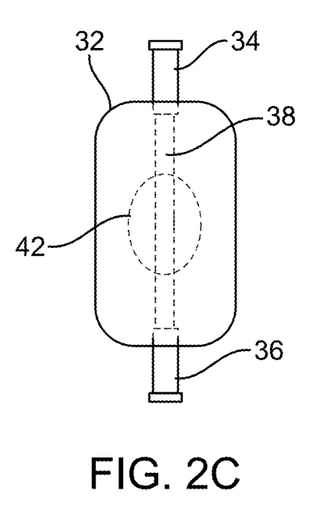
Figure 2D:
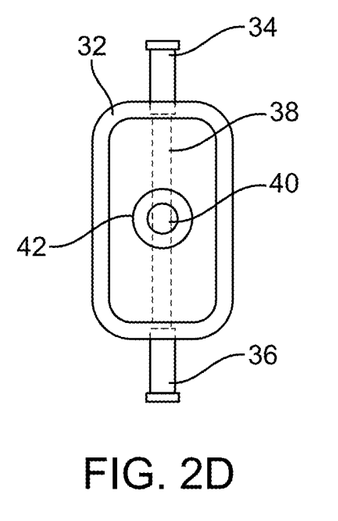

One variation of the apparatus is illustrated in the perspective view of FIG. 1 which shows assembly 10 which may be used to effectively concentrate one or more plasma constituents and/or cells from blood plasma or PRP without requiring centrifugation. The assembly 10 may concentrate the constituents and/or cells with or without white blood cells. As shown, a first reservoir or syringe 22 may be fluidly coupled to a second reservoir or syringe 26 via a manifold 12 which also provides receiving channels to temporarily or permanently secure the tips of the respective syringes 22, 26 to the manifold 12. While syringes are shown and described, alternative fluid container or reservoir configurations may be used instead. Each of the syringes 22, 26 may be integrated directly with the manifold 12 or optionally fitted with non-standard couplings to ensure that one or both syringes 22, 26 cannot be inadvertently detached or attached to an incorrect port.

A fluid channel 16 may extend through the manifold 12 to fluidly couple the openings of the first syringe 22 and second syringe 26 and a withdrawal channel 18 may extend through the manifold 12 to fluidly couple to the fluid channel 16 which may have a diameter of, e.g., 5 mm, but may range anywhere from, e.g., 3 to 10 mm. An actuatable valve 20 which may be configurable between an open and closed configuration, e.g., automatically or manually via a stopcock, may be incorporated with the withdrawal channel 18 to prevent the release of fluid from the fluid channel 16. A filter or frit 14 may also be incorporated into the manifold 12 at the entry of the withdrawal channel 18 to filter select components from passing into the withdrawal channel 18 from the fluid channel 16.

The fluid channel 16 may optionally incorporate a number of projections or features such as vanes, spikes, crosshairs, etc., to facilitate the effective mixing of fluids as they pass through the fluid channel 16. Additionally, a volume of desiccating beads or elements may also be added within the fluid channel 16 or directly within one or both of the syringes 22, 26. With the volume of desiccating beads or elements included within the fluid channel 16 or directly within one or both of the syringes, the device be optionally tapped or shaken or otherwise moved while being held in a horizontal configuration in order to facilitate the dispersion of the volume of desiccating beads over the bottom of the connecting channel 16 or within the syringes 22, 26 before introducing the material to be concentrated. Doing so may reduce the likelihood of forming any clumps immediately upon introduction of the plasma or PRP into contact with the beads.

A volume of blood plasma or PRP to be concentrated may be introduced within the first syringe 22 or second syringe 26 (or both) and the syringes 22, 26 may be coupled to their respective ends in the manifold 12 such that their openings are positioned at each end of the fluid channel 16. With the volume of desiccating beads retained within the fluid channel 16 and/or within one or both syringes 22, 26, the respective plungers 24, 28 may be actuated in an alternating manner to push the blood plasma or PRP back-and-forth between the syringes 22, 26 through the fluid channel 16. As the blood plasma or PRP is cycled between the syringes 22, 26, the withdrawal channel 18 may remain closed to prevent leakage from the fluid channel 16. As the blood plasma or PRP cycles between the syringes 22, 26 through the fluid channel 16, it may become concentrated as the volume of beads mixes thoroughly with the blood plasma or PRP and absorbs various components within the blood plasma or PRP such as water, electrolytes and small proteins, thus leaving a platelet-rich plasma concentrate. Because the mixture of the beads and blood plasma or PRP is cycled back-and-forth between the syringes 22, 26, the syringe connections to the manifold 12 may be integral to ensure a fluid-tight connection and the internal diameter of the syringe couplings may be tapered internally at their proximal ends, e.g., to a diameter (2 to 6 mm) relatively smaller than the syringe bore but relatively larger than a standard syringe barrel bore to reduce the likelihood of clogging due to any bead clumps which may be formed by gel polarization.

Once the blood plasma or PRP has been sufficiently concentrated, the valve 20 along the withdrawal channel 18 may be opened to allow for the withdrawal of the concentrated product as it passes through the fluid channel 16. The filter or frit 12 may prevent the passage of the beads or other components into the withdrawal channel 18 thus allowing only the concentrated product to pass through withdrawal channel 18 and into a reservoir such as a collection syringe. The withdrawal channel 18 may be opened to allow for the removal of the concentrated product as the bead and blood plasma or PRP mixture continues to cycle through the fluid channel 16. This ensures that the concentrated product may be harvested uniformly from the mixture. Also, sweeping of the bead surfaces during product extraction further ensures that if the beads are not yet fully saturated, any residual water absorption does not cause gel polarization and loss of macromolecular constituents or clumping.

Alternatively, both plungers 24, 28 in each respective syringe 22, 26 may be simultaneously pressed to create pressure to force the concentrated product from both syringes 22, 26 and through the withdrawal channel 18 for collection with the valve 20 opened. In any case, the filter or frit 14 may prevent the beads from passing into the withdrawal channel 18 so that only the concentrated product may pass through.

In an alternative variation, an additional withdrawal channel and port may be provided so that the material can be introduced without having to pass through the filter or frit 14. As the material is introduced through the manifold 12, it may mix with the beads contained within and sweep them into one or both of the syringes 22, 26 forcing the respective plungers 24, 28 to extend partially.

These beads may function as a concentrator when contacting and mixing with the blood plasma or PRP and may comprise any number of materials which are configured to selectively absorb particular components such as water, electrolytes, small proteins, etc. leaving a concentrated product for collection. Examples of various materials that the beads may be fabricated from may include any suitable material for processing the biological materials such as various polymers, metals, minerals, polysaccharides, silica gel, ceramics, glasses, etc.

Various examples of polymers may include, e.g., dextranomer, polystyrene, polyethylene, polyvinyl chloride, polypropylene, polyacrylamide, etc. Various examples of metals may include, e.g., titanium, etc., while various examples of minerals may include, e.g., zeolites, corundum, quartz, etc. Various examples of polysaccharides may include, e.g., alginate gel, starch, dextran, agarose, etc.

In some variations, the beads may be conjugated with an activating material such as an antibody such as immunoglobulin g.

Because the beads are used to concentrate the blood plasma or PRP by inducing a change in the biological material, the size and composition of the beads can be varied depending upon the bead materials used and the biological material to be concentrated. In one example, the beads may be comprised of a polyacrylamide material (e.g., Bio-Rad P6 chromatography beads having a nominal molecular weight limit (NMWL) of 1,000-6000) and may be sized to each have a dry bead diameter of, e.g., 45 to 90 micron. Hence, for a given volume of blood plasma or PRP to be concentrated such as about 10 ml, although the volume may range anywhere from, e.g., 5 to 30 ml, the amount of beads used may be about 1,000 mg although the amount may range anywhere from, e.g., 200 to 5,000 mg, in weight or at ratio of beads to blood plasma or PRP may be about 0.1 but may range anywhere from, e.g., 0.04 to 0.15, to effectively separate out the desired components.

Furthermore, depending upon the beads and the biological material to be concentrated, the number of back-and-forth cycles between the syringes 22, 26 can vary. In one variation, the blood plasma or PRP may be cycled, e.g., 10 to 50 cycles, to sufficiently mix the beads with the blood plasma or PRP. Alternatively, the cycling may be timed to allow for sufficient mixing and may range from, e.g., 30 sec. to 2 min. or longer. Additionally, with the diameter of the fluid channel 16 being relatively small relative to the size of the beads, any clumps which may form due to imperfect mixing may be broken apart by turbulence and shear as the clumps pass through the channel 16. Moreover, the method of cycling back-and-forth between the syringes 22, 26 facilitates an efficient mixing of beads with the blood plasma or PRP to produce a more uniform slurry with relatively less frothing.

FIGS. 2A to 2D show perspective, side, bottom, and top views, respectively, of another manifold variation which may be used with conventional syringes or modified syringes. The manifold 30 may include a manifold body 32 which includes respective ports 34, 36 positioned on opposite ends of the manifold body 32 for fluidly connecting to one another via fluid channel 38 extending through the manifold body 32 and between the ports 34, 36. A withdrawal channel 40 may extend from the fluid channel 38 through a filter or fit 42 positioned to prevent or inhibit any beads or other components from passing through and into the withdrawal channel 40.

Although the withdrawal channel 40 is shown extending transversely relative to the fluid channel 38, the withdrawal channel 40 may be angled at a non-normal angle relative to the fluid channel 38 instead. Moreover, the assembly 30 may be used with conventional syringes while in other variations the ports 34, 36 may be keyed or modified to engage temporarily or permanently with specially configured syringes.

Example 1

Figure 3A:
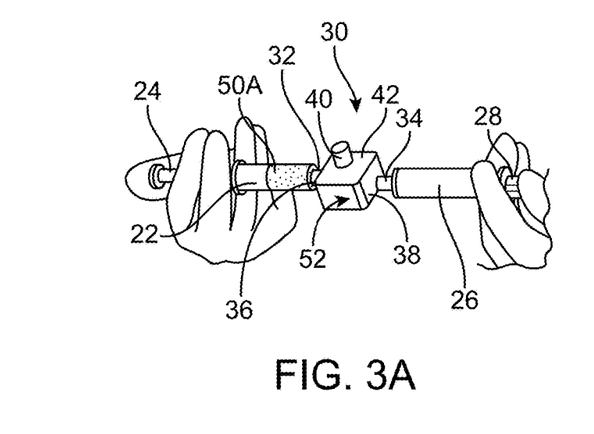
FIGS. 3A to 3E show perspective views of one example for concentrating plasma or PRP.

In one example of a test which was performed, a first volume 50A of citrated bovine PRP was introduced directly into the first syringe 22 which was coupled to port 36 and the withdrawal channel 40 outlet was sealed via a cap, as shown in the perspective view of FIG. 3A. A second syringe 26 with its plunger 28 fully depressed was coupled to the port 34 and a volume of concentrating beads 52 was preloaded into the fluid channel 38 contained within manifold body 32 prior to attaching the PRP-loaded first syringe 22.

Figure 3B:
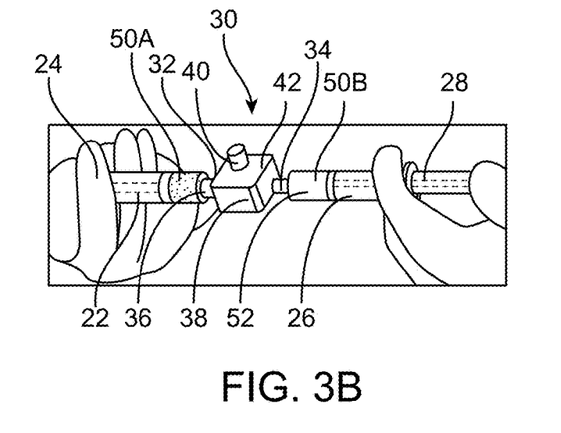

The first plunger 24 was depressed forcing the first volume 50A of PRP to pass into the fluid channel 38 and into contact with beads 52 contained within. As the first volume 50A is further introduced, the PRP and beads may begin mixing as they are swept into the opposed second syringe 26 to capture a second volume 50B while forcing the second plunger 28 to expand, as shown in the perspective view of FIG. 3B.

Figure 3C:
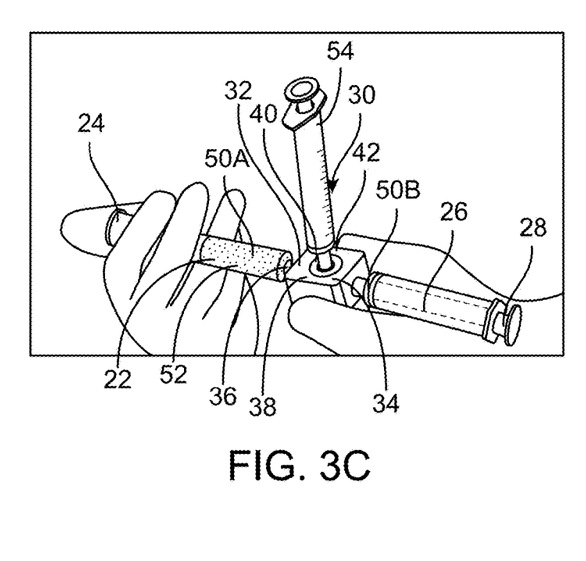
Figure 3D:
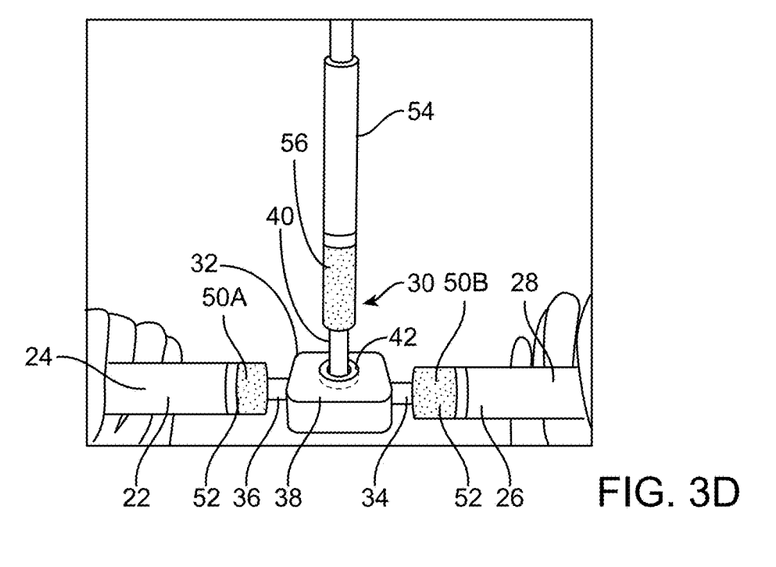

The process of gently cycling the PRP back-and-forth between the syringes 22, 26 through the manifold body 32 may be maintained for a period of time, e.g., about 30 sec., to allow for the beads 52 to sufficiently absorb water from the plasma. Once the mixing is completed, the resulting concentrated mixture may appear as a uniform slurry with no bead clumps visible. The cap (or valve, if present) may be removed and a collection syringe 54 may be attached to the withdrawal port 40 with its plunger fully depressed, as shown in the perspective view of FIG. 3C. The cycling may be continued between the first and second syringes 22, 26 while the concentrated product 56 may be forced to pass through the filter or frit 42, which prevents the beads from passing, by the modest pressure generated by the flow restriction and resistance of the syringes 22, 26. This pressure may force the concentrated PRP through the bead-retaining filter or frit 42 and into the collection syringe 54, as shown in the perspective view of FIG. 3D.

Figure 3E:
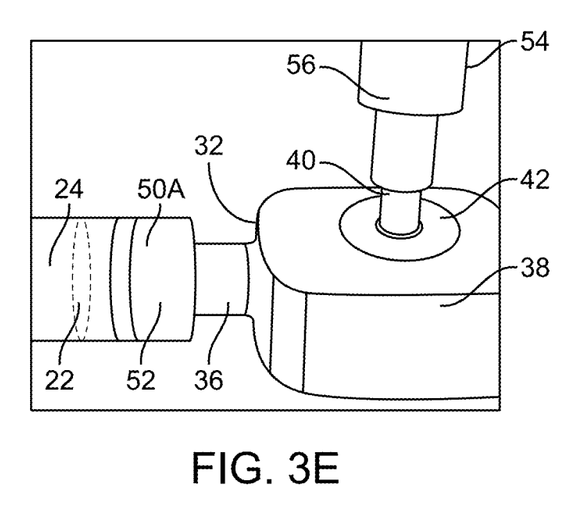

When the bulk of concentrated fluid 56 had been expressed through the filter or fit 42 into the collection syringe 54, the remaining bead pack 52 may appear uniform and white, indicating that the mixing and harvesting had maintained uniformity of the slurry and that concentrated fluid 56 had been almost entirely transferred out into the collection syringe 54, as shown by the perspective view of FIG. 3E.

Example 2

Figure 4A:
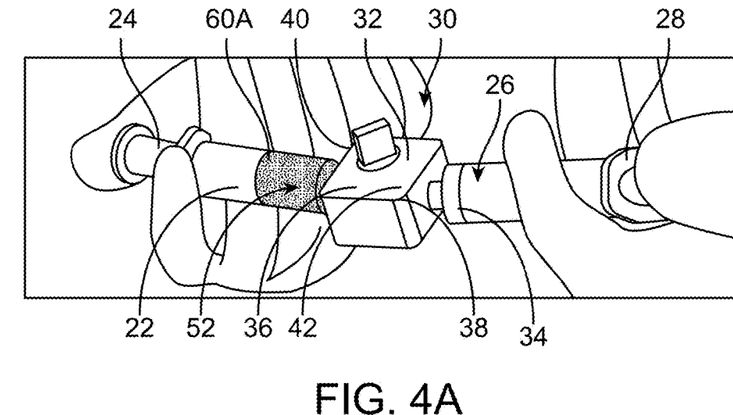
FIGS. 4A to 4D show perspective views of another example for concentrating a volume of buffy coat.

In another example of a test which was performed, a volume of buffy coat 60A comprised of plasma, platelets, white blood cells, and a small amount of red blood cells was introduced into the first syringe 22 which was coupled to port 36 opposite to the second syringe 26 which was coupled to port 34 with its plunger 28 fully depressed, as shown in the perspective view of FIG. 4A.

Figure 4B:
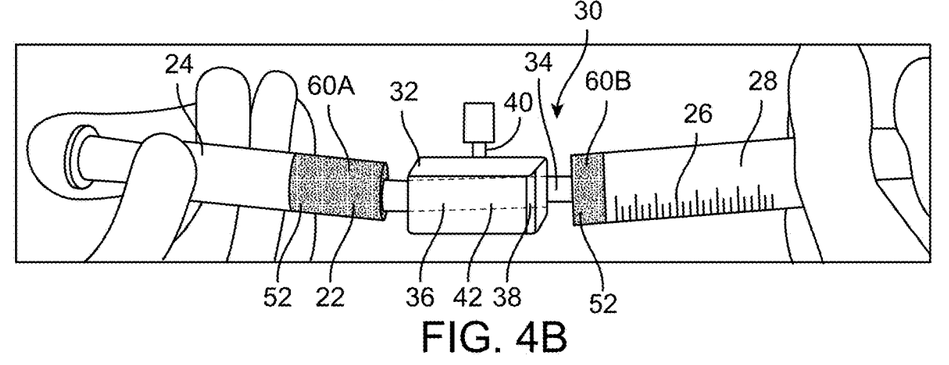

An amount of the beads 52 was preloaded into the first syringe 22 with the volume of buffy coat 60A although the beads 52 may be alternatively preloaded within the fluid channel 38 of the manifold body 32. The volume of buffy coat was then cycled between the syringes 22, 26 through the fluid channel 38 to thoroughly mix the beads 52 between the volumes 60A, 60B, as shown in the perspective view of FIG. 4B. In order to prevent clumping of the beads 52 (such as when first contacted by the fluid), the volume may be quickly cycled between the syringes 22, 26 particularly when the beads 52 are preloaded directly within one of the syringes.

Figure 4C:
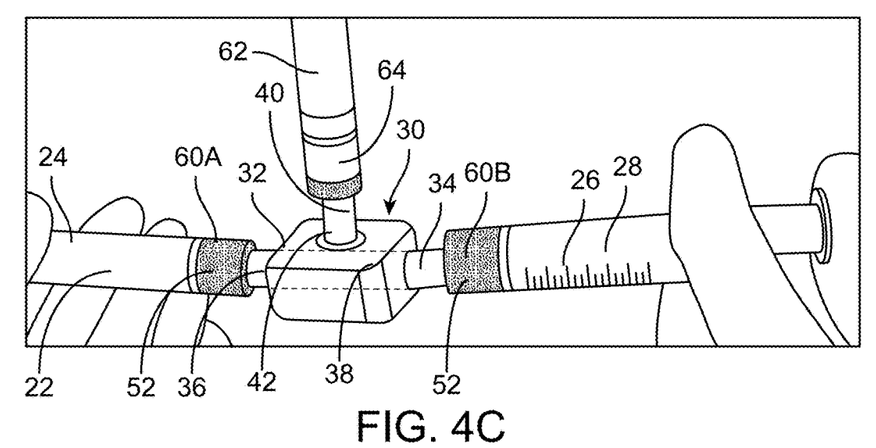

After a period of time, e.g., about 30 seconds, of cycling the mixed slurry back-and-forth between the syringes 22, 26, a collection syringe 62 was attached to the outlet port 40 and concentrated product 64 was expressed though the bead-retaining filter or frit 42 into the collection syringe 62 by continuing to pass the slurry back-and-forth between the in-line syringes 22, 26, as illustrated in the perspective view of FIG. 4C.

Figure 4D:
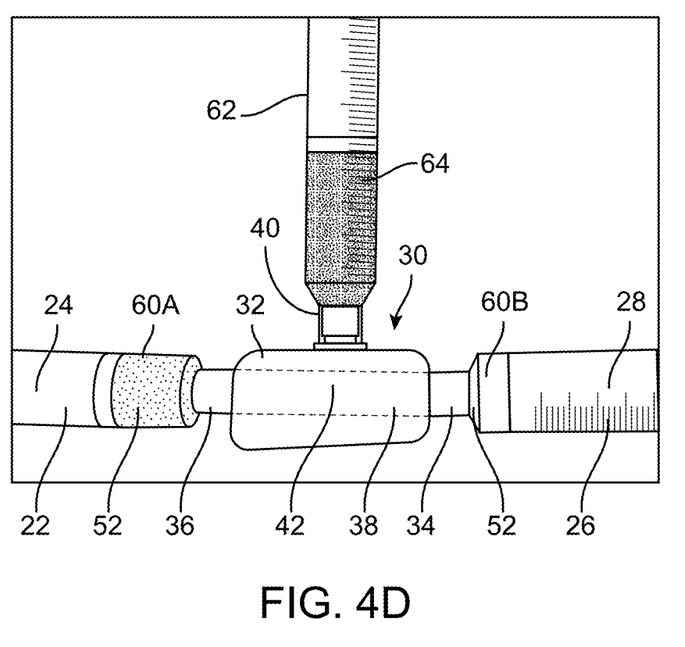

After concentrated product 64 was collected, the remaining bead pack 52 may appear uniform and slightly pink in color from traces of red blood cells in the small remaining volume of fluid interstitial between the packed beads 52. FIG. 4D illustrates a perspective view showing how the concentrated product 64 is collected while the beads 52 may remain within the first syringe 22 and/or second syringe 26.

As shown by both examples above, in concentrating PRP and the buffy coat, the ratio of the volume recovered to initial input volume was consistent with the amount of water expected to be absorbed by the amount of beads 52 employed. This indicated an effective concentration of cells and macromolecules. In separate preliminary testing, cell counts were conducted and confirmed that cell recoveries were relatively high.

Alternative Configurations

Figure 5:
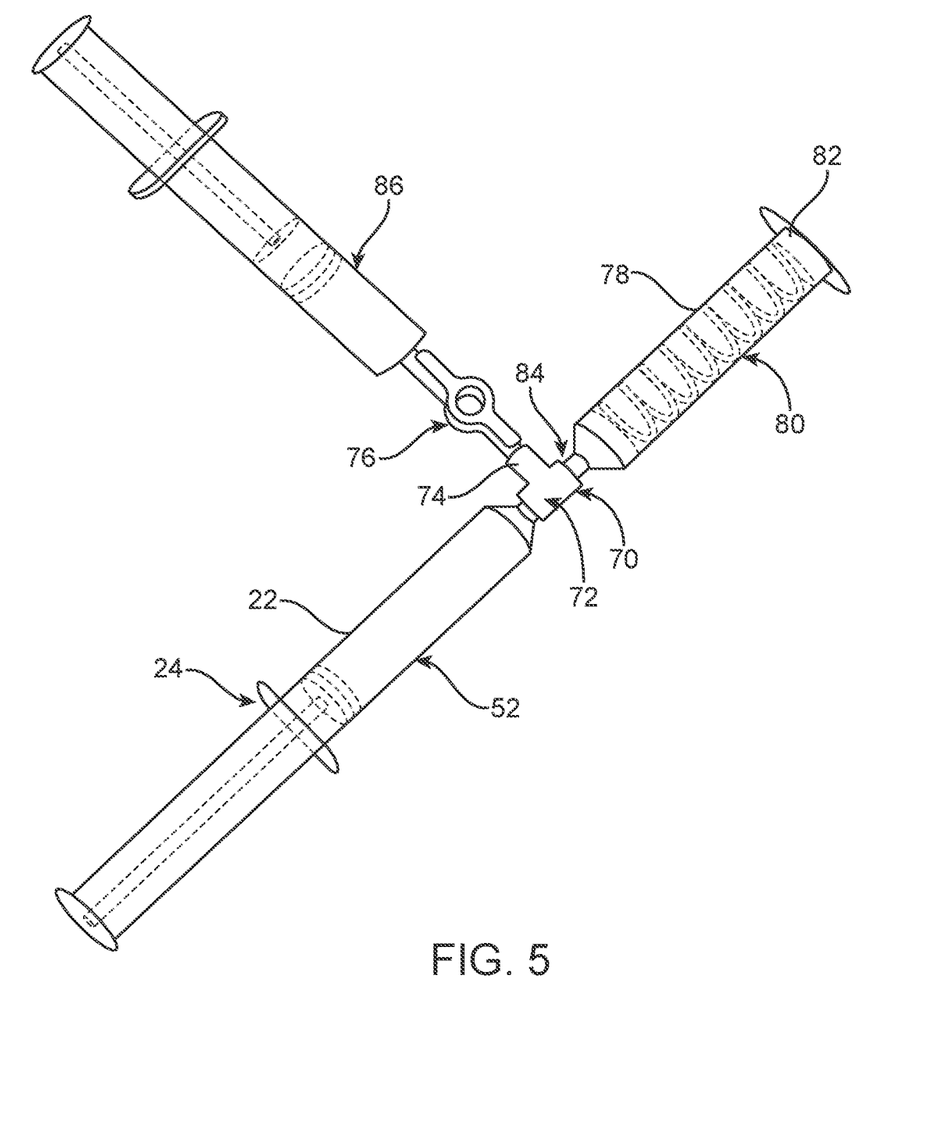
FIG. 5 shows a perspective view of another variation of an apparatus which may utilize applying and releasing pressure with a single syringe.

A number of optional configurations are possible, for example, one of the two in-line syringes may be fitted with a biasing element such as a spring so that mixing can be effectuated by alternately applying and releasing pressure on only one syringe. The two syringes need not be parallel, but may be connected via a connecting manifold which adjoins them at any angle relative to each other. The perspective view of FIG. 5 shows a syringe 22 coupled to a manifold body 70 containing a filter or frit 72. The second modified syringe 78 may be coupled to the opposing port of the manifold body 70 but rather than having a plunger, the second syringe 78 may contain the biasing element 80 within and anchored between the movable plunger and an anchoring platform 82 which may be securely positioned relative to the body of the syringe 78.

The biasing element 80 may maintain the plunger in a compressed state such that the plunger is biased to push away from the anchoring platform 80. With this configuration, the first syringe 22 may contain the beads 52, as shown, or the manifold body 70 may contain the beads 52. In either case, the blood plasma or PRP may be introduced into the first syringe 22 and the plunger 24 may be depressed to force the mixture of the beads 52 and blood plasma or PRP through the fluid channel of the manifold body 70 and into the second syringe 78. The plunger 24 of the first syringe 24 may be released to allow for the biasing element 80 to automatically push the plunger within the second syringe 78 to force the mixture back through the manifold body 70 and back into the first syringe 22. This process may be repeated, as described herein, until the fluid has been sufficiently concentrated. The stop cock 76 or valve (if present) may be opened to allow for the concentrated product to pass through the filter or frit 72 and through the withdrawal channel 74 and into the attached collection syringe 86.

Figure 6:
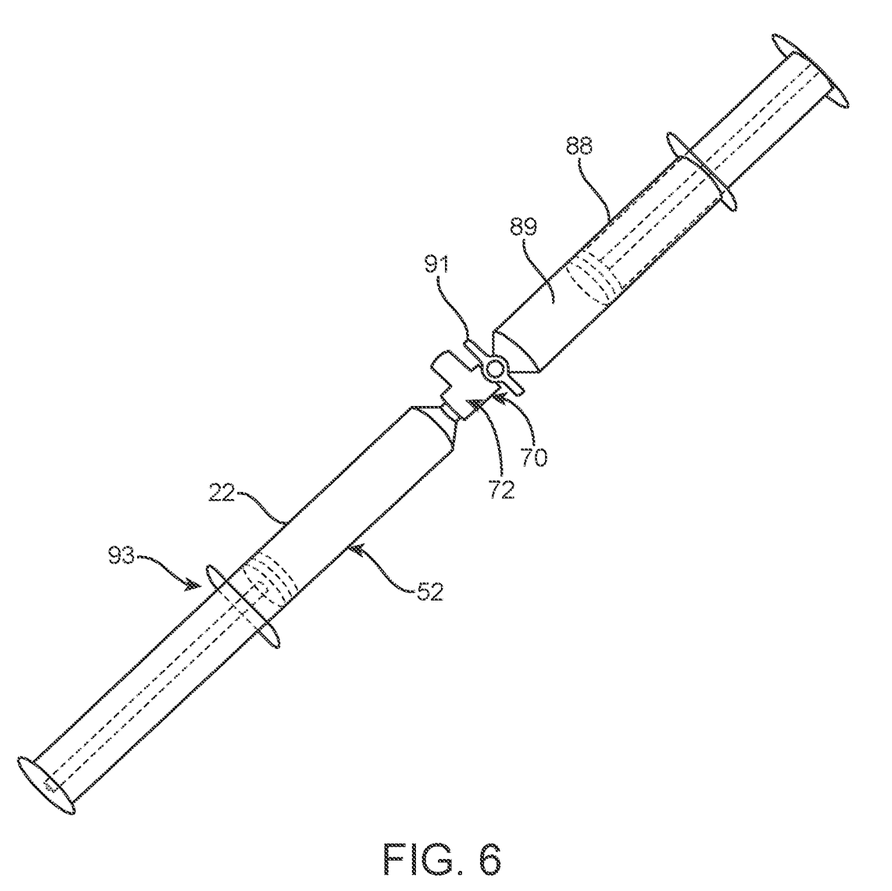
FIG. 6 shows a perspective view of another variation of an apparatus which may utilize a vacuum force created in one of the syringes to quickly mix the beads with plasma or PRP.

In yet another embodiment as shown in the perspective view of FIG. 6, a volume of blood plasma or PRP may be concentrated by connecting a first syringe 22 to a second syringe 88 via a manifold 70 containing a filter or frit 72, as previously described. The first syringe 22 may be optionally preloaded with a volume of beads 52 while the second syringe 88 may contain a volume of blood plasma or PRP 89 to be concentrated. In other variations, the volume of beads 52 may instead be preloaded within the manifold 70 itself. The manifold 70 or the second syringe 88 may include a valve 91 such as a stopcock which may be initially closed to prevent communication between the first and second syringes 22, 88 when initially coupled to the manifold 70.

With the plunger of the first syringe 22 initially fully depressed, the plunger may be pulled proximally with the valve 91 closed such that a vacuum force is created within the first plunger 22. This also allows for the volume of beads 52 contained within to be dispersed within the syringe 22 prior to contacting the fluid contained within the second syringe 88. The first plunger may be locked into its retracted position via a locking mechanism 93 and the valve 91 may be opened so that the vacuum within the first syringe 22 may pull the fluid 89 in through the manifold 70 from the second syringe 88. This sudden dispersion of fluid 89 into the first syringe 22 may help to minimize any likelihood of clumping of the beads 52 within the first syringe 22 upon initial fluid contact and may also facilitate the rapid introduction of the fluid 89 after the valve 91 is opened.

Once the fluid 89 has been introduced into the first syringe 22, the locking mechanism 93 may be released (e.g., by twisting the plunger rod relative to the syringe body) and the cycling of the slurry between the two syringes 22, 88 may be accomplished. A collection syringe may be subsequently coupled to the manifold 70 for withdrawal, as previously described. Similarly, the syringes 22, 88 may be attached via a straight connector or a connector which adjoins the two syringes at any angle relative to each other.

Figure 7A:
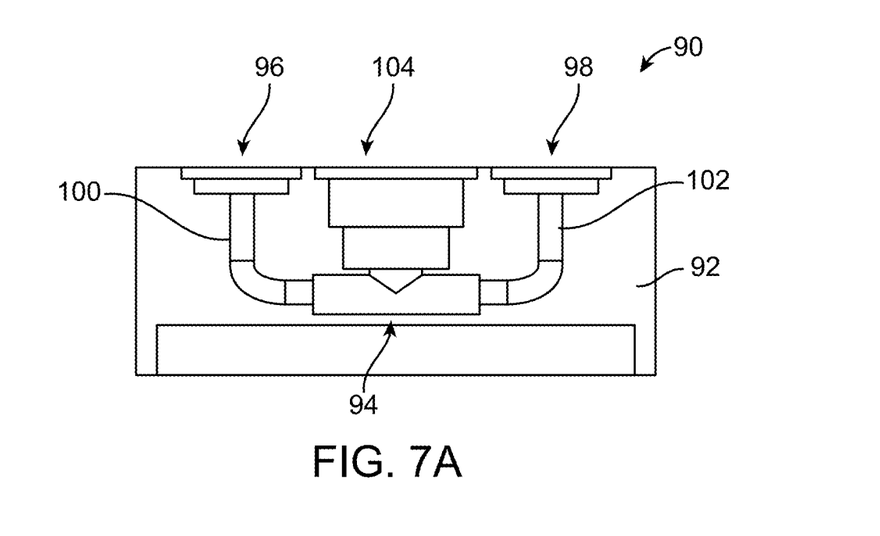
FIGS. 7A and 7B show partial cross-sectional side and perspective views of a manifold which allows for the two syringes to be fluidly coupled to one another at various angles.
Figure 7B:
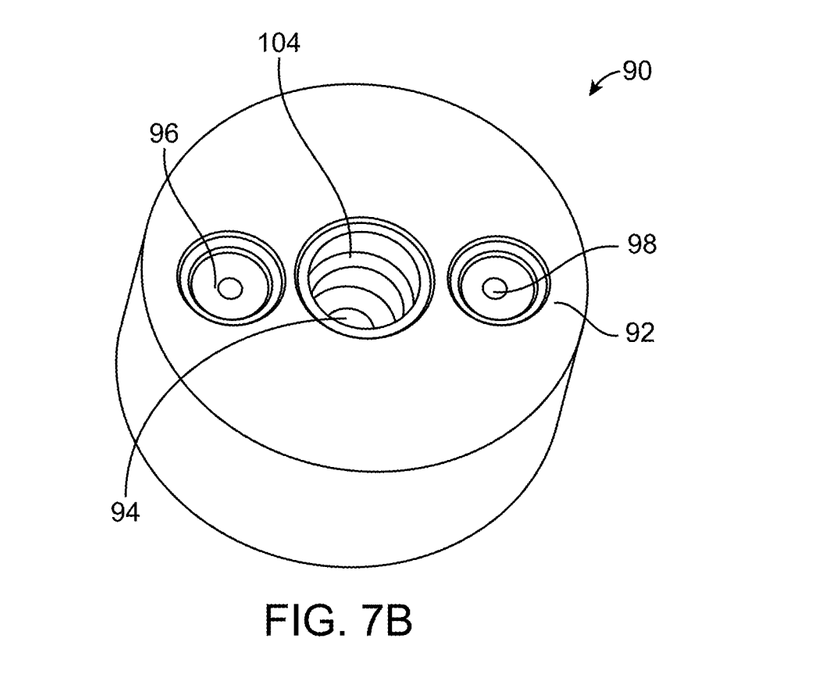

FIGS. 7A and 7B show partial cross-sectional side and perspective views of a manifold 90 which allows for the two syringes to be fluidly coupled to one another at various angles. As shown, the manifold body 92 may have a first port 96 and a second port 98 both positioned along a first surface of the manifold 92 such that the ports 96, 98 are in proximity to one another and fluidly connected via curved or angled fluid channels 100, 102. An optional chamber 94 may be incorporated between the fluid channels 100, 102 for holding a volume of beads 52 within during the initial mixing phase between the syringes. Additionally, a filter or frit well 104 may also be defined to extend from the chamber 94 for retaining the frit within the chamber 94 as well as allowing for a withdrawal syringe to be coupled to the manifold body 92.

Because the ports 96, 98 are located along a common surface of the manifold body 92, the syringes may be angled relative to one another and relative to the manifold body 92 in any number of angles. Furthermore, this variation may be utilized with any of the devices and methods described herein.

Additionally, in any of these variations described herein, the product collection syringe (or other collection vessel, such as a centrifuge tube integrating a frit above a distal volume of receiving space) could be subjected to centrifugation to centrifugally drive the concentrate through the fit, separating it from the bead pack. This may have the advantage of improving volume recovery, by driving all interstitial fluid between the beads out of the bead pack although this would required an extra transfer step and a centrifuge.

Yet another alternative to pressure applied to the slurry for recovering the concentrated product is to blow the concentrated product out of the bead pack through a fit with, e.g., a steam of air. This affords a good volumetric recovery requires a source of pressurized air. Furthermore, it may also result in frothing and potential damage to cells and plasma proteins if not done with care.

With regard to volume recovery, it should be noted that with close packing of the beads, about ⅓ of the total pack volume is comprised of interstitial space. By squeezing out the concentrated fluid under pressure, this volume may not be recoverable. Regardless of the method (pressure or centrifugation) used to recover the concentrate, fold concentration may be limited to about 3 times due to the difficulty of effectively mixing a slurry comprising a volume ratio of (fully swollen) beads to residual interstitial fluid greater than two. A reasonable volumetric recovery of product harvested by pressure may be on the order of, e.g., 1.5 to 2 times.

Figure 8:
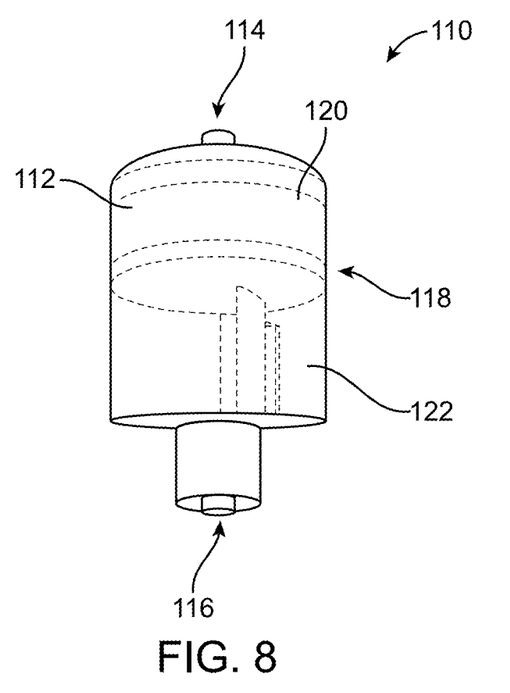
FIG. 8 shows a perspective view of a coupling which may be used in combination with a centrifuge.

In yet another variation for recovering a volume of concentrated product, the coupling 110 shown in FIG. 8 may be used in combination with a centrifuge rather than withdrawing the concentrated product directly from the manifold. The coupling 110 may have a housing 112 with an introduction port 114, such as a Luer connector, positioned upon an upper portion of the housing 112 into which a mixed slurry may be introduced. A withdrawal port 116, such as a Luer connector, may be positioned upon a lower portion of the housing 112 and a fit 118 may be positioned within the housing 112 to separate the internal volume into an upper portion 120 and a lower portion 122.

With the mixed slurry introduced through port 114 and into the upper portion 120 of housing 112, both ports 114, 116 may be capped or closed and entire coupling 110 may undergo centrifugation to drive the fluid from the upper portion 120, through the fit 118, and into the lower portion 122 of housing 112. Once all concentrated product has been separated into the lower portion 122 and the beads remaining within the upper portion 120 above the fit 118, the withdrawal port 116 may be opened to withdraw the concentrated product from the housing 112.

Figure 9A:
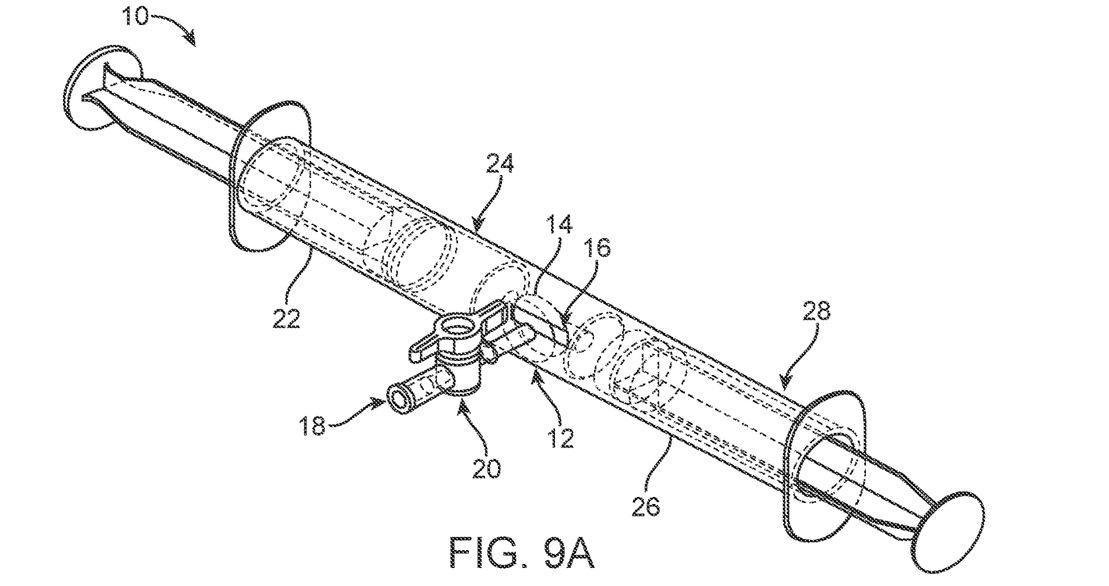
FIGS. 9A to 9C show one example of how a volume of blood plasma or PRP may be mixed with a desiccant and then centrifuged to result in a concentrated product.
Figure 9B:
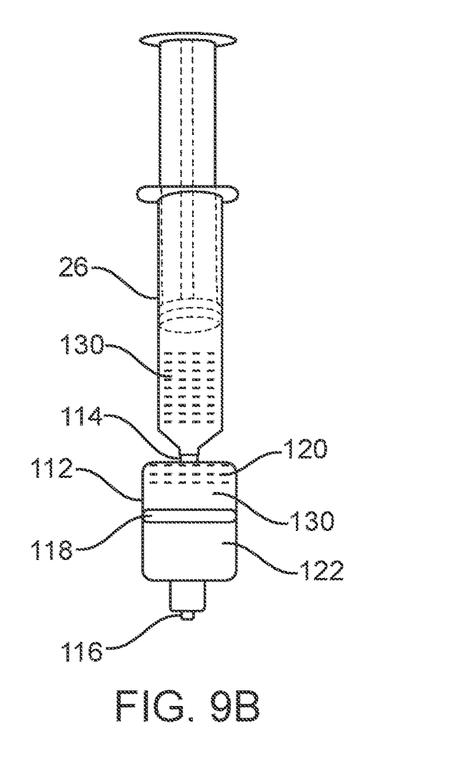

In one example of use for the housing 120, a manifold 12 may be coupled to respective syringes 22,26 to initially mix the volume of blood plasma or PRP with a volume of desiccating beads which may freely intermix with the volume of blood plasma or PRP as it is passed between the syringes 22,26, as described above and as shown in FIG. 9A. The resulting slurry or mixture 130 of blood plasma or PRP and desiccating beads may be transferred to a single syringe 26 which may be decoupled from the manifold 12 and then fluidly coupled to the introduction port 114. The slurry or mixture 130 from the syringe 26 may then be transferred through the introduction port 114 and into the upper portion 120 of housing 112, as shown in FIG. 9B.

Figure 9C:
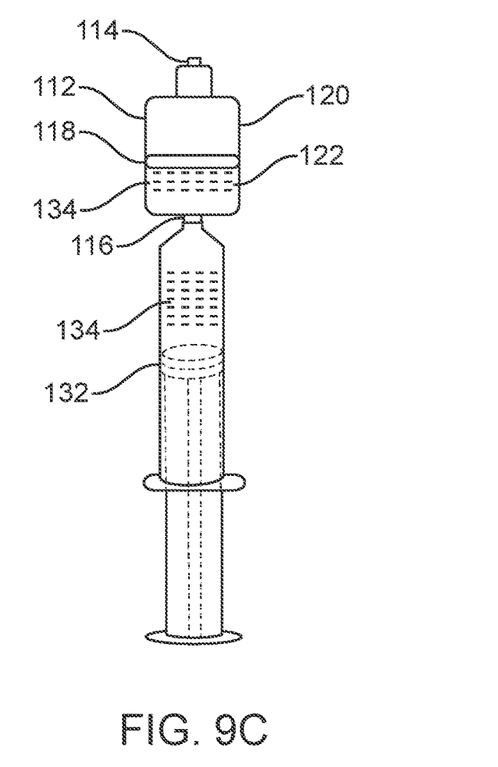

Once the slurry or mixture 130 has been sufficiently transferred, the syringe 26 may be decoupled from the introduction port and housing 112 may then undergo centrifugation to drive the slurry or mixture 130 from the upper portion 120, through the frit 118, and into the lower portion 122 of housing 112. The frit 118 may retain the desiccating beads having absorbed one or more components from the blood plasma or PRP such that the resulting concentrated product 134 may be retained within the lower portion 122. An additional syringe 132 may be fluidly coupled to the withdrawal port 116 to then withdraw the concentrated product 134 from the lower portion 122 and into the additional syringe 132, as shown in FIG. 9C.

The apparatus and methods disclosed above are not limited to the individual embodiments which are shown or described but may include combinations which incorporate individual features between the different variations. Modification of the above-described assemblies and methods for carrying out the invention, combinations between different variations as practicable, and variations of aspects of the invention that are obvious to those of skill in the art are intended to be within the scope of the claims.

What is claimed is:

1. An apparatus for concentrating constituents from a fluid, comprising:
   a connector body in fluid communication with a fluid channel;
   a first reservoir having a variable pressure;
   a second reservoir having a variable pressure, wherein the first reservoir is fluidly coupled to the second reservoir through the connector body while maintained at an angle relative to the second reservoir, wherein the connector body is sized to flow a desiccant between the first reservoir and the second reservoir;
   a biasing element positioned inline with the second reservoir and configured to provide a pressure against a plunger within the second reservoir;
   a withdrawal channel in fluid communication with the fluid channel; and
   a filter positioned within the connector body to prevent passage of the desiccant from the fluid channel into the withdrawal channel.

2. The apparatus of claim 1 wherein the connector body comprises a manifold body.

3. The apparatus of claim 1 wherein the first reservoir and second reservoir each comprise a syringe having a plunger.

4. The apparatus of claim 1 further comprising a valve in communication with the withdrawal channel.

5. The apparatus of claim 1 wherein the filter comprises a frit.

6. The apparatus of claim 1 further comprising a volume of desiccant beads for introduction into the first or second reservoir.

7. The apparatus of claim 1 wherein the biasing element comprises a spring element.

8. The apparatus of claim 1 wherein the first reservoir further comprises a locking mechanism configured to maintain a position of a plunger within the first reservoir to create a vacuum force.

* * * * *